(12) United States Patent
Ando et al.

(10) Patent No.: US 6,444,827 B2
(45) Date of Patent: Sep. 3, 2002

(54) PRODUCTION METHOD OF ISOXAZOLIDINEDIONE COMPOUND

(75) Inventors: Koji Ando, Takatsuki; Masanobu Suzuki, Asaka, both of (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/839,215

(22) Filed: Apr. 23, 2001

Related U.S. Application Data

(62) Division of application No. 09/424,711, filed as application No. PCT/JP99/01434 on Mar. 19, 1999, now Pat. No. 6,248,897.

(30) Foreign Application Priority Data

Mar. 30, 1998 (JP) .......................................... 10-104098

(51) Int. Cl.⁷ .......................................... C07D 263/32
(52) U.S. Cl. ..................................................... 548/235
(58) Field of Search ......................................... 548/235

(56) References Cited

U.S. PATENT DOCUMENTS

| 4,602,027 | A |   | 7/1986 | Meguro et al. |   |
| 5,728,720 | A |   | 3/1998 | Shinkai | 514/374 |
| 5,753,681 | A |   | 5/1998 | Sohda et al. | 514/376 |
| 5,763,467 | A |   | 6/1998 | Goldstein et al. | 514/374 |
| 5,932,601 | A |   | 8/1999 | Sohda et al. | 514/376 |
| 6,248,897 | B1 | * | 5/2001 | Ando et al. |   |

FOREIGN PATENT DOCUMENTS

| EP | 177 353 | 4/1986 |
| EP | 544 696 | 6/1993 |
| EP | 796618 | 9/1997 |
| JP | 58 219169 | 12/1983 |
| JP | 5 508654 | 2/1993 |
| JP | A-7-188227 | 7/1995 |
| WO | 95/18125 | 7/1995 |

OTHER PUBLICATIONS

Accession No. 2001:416908, compounds RN 341986–88–7, RN 341987–21–1, RN 341987–67–5, and RN 341987–86–8; Accession No. 1979:6388, compounds RN 68430–55–7, RN 68430–56–8, RN 68430–64–8, and RN 68430–65–9; and Accession No. 1978:89653.*

Meguro et al., Chem. Pharm. Bull, vol. 34, No. 7, "Studies on Antidiabetic Agents VII . . . Acid Derivatives", pp. 2840–2851, 1986.

Abstract: A. Rosowsky et al., "Side chain modified . . . 8–dideazafolic acid", J. Med. Chem., vol. 35:14, pp. 2626–2630, 1992.

Abstract: H. Shinkai, "Isoxazolidine–3,5–dione . . . Hypoglycemic Agents", J. Med. Chem., vol. 41:11, 1853–64, 1992.

T. Sohda et al., "Studies on Antidiabetic Agents . . . Hypolipidemic Agents", J. Med. Chem., vol. 35:14, pp. 2617–2626, 1992.

Abstract: H. Shinkai, "The isoxazolidine–3,5–dione . . . insulin sensitizers", Drugs Future, vol. 24:8,. pp. 893–898, 1999.

Derwent Abstract for JP–A–7–188227, 1995.

* cited by examiner

*Primary Examiner*—Ceila Chang
*Assistant Examiner*—Sonya Wright
(74) *Attorney, Agent, or Firm*—Foley & Lardner

(57) ABSTRACT

The present invention relates to a novel method for producing an intermediate compound [6]

[6]

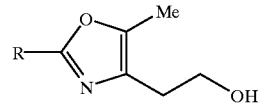

wherein R is as defined above, at high yield.

1 Claim, No Drawings

PRODUCTION METHOD OF ISOXAZOLIDINEDIONE COMPOUND

This application is a DIV of Ser. No. 09/424,711 filed Nov. 29, 1999, now U.S. Pat. No. 6,248,897, which is a 371 of PCT/JP99/01434 filed Mar. 19, 1999.

TECHNICAL FILED

The present invention relates to a novel method for producing a compound of the formula [11]

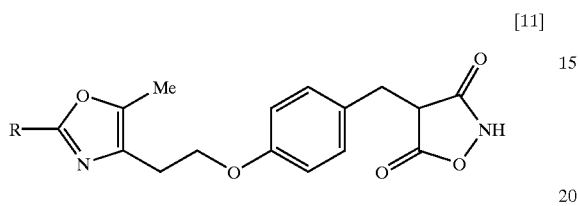

wherein R is an optionally substituted aromatic hydrocarbon group, an optionally substituted alicyclic hydrocarbon group, an optionally substituted heterocyclic group or an optionally substituted condensed heterocyclic group, which is useful as a therapeutic agent for diabetes, and a method for producing an intermediate for producing this compound [11].

BACKGROUND ART

The above-mentioned compound [11] useful as a therapeutic agent for diabetes, an intermediate and a method for producing them have been already disclosed in the specification of WO95/18125, and an intermediate compound [6']

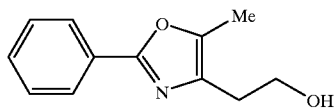

and a method for producing same have been specifically disclosed in Journal of Medicinal Chemistry, 1992, Vol. 35, No. 14, 2625.

However, these conventional production methods require many steps and the yields of the final product and intermediates therefor are not sufficiently satisfactory. In addition, solvent, base, catalyst and the like to be used in each step suffice for use at laboratory levels but many of them are problematically impractical and cannot be used in industrial production.

DISCLOSURE OF THE INVENTION

Therefore, many attempts have been made in each step to solve such problems. To be specific, Steps 1–4 of the method (hereinafter to be referred to as A method) disclosed in Journal of Medicinal Chemistry, 1992, Vol. 35, No. 14, 2625, which is the production method most similar to the inventive method, were considered.

In A method, for example, compound [6'] wherein R is phenyl, which is one of the intermediates in the present invention, is produced by the following Steps 1 to 4.

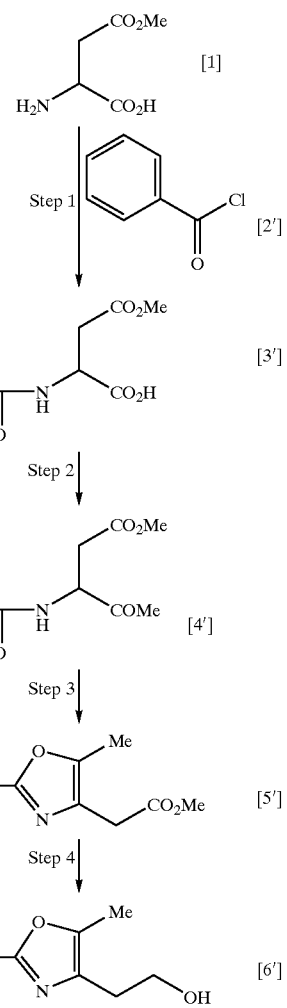

Step 1

According to A method, compound [1] is reacted with compound [2'] in dichloromethane in the presence of triethylamine to give compound [3']. Dichloromethane used here as a solvent is impractical for industrial production because a large amount thereof after use cannot be drained out by regulation. The present inventors have found that a safe and economical aqueous solvent (particularly water) can be also used for this reaction and solved this problem. Surprisingly, the use of an inorganic base, such as potassium carbonate, sodium carbonate and the like, as a base here was also found to increase the yield to 92–97%. Consequently, the yield could be increased by 10% as compared to conventional methods.

Step 2 and Step 3

According to A method, compound [3'] is reacted in 10 equivalents of acetic anhydride in the presence of 6–7 equivalents of triethylamine using dimethylaminopyridine to give compound [4']. However, an aftertreatment step is necessary for obtaining compound [4'], which comprises adding water to the solvent, acetic anhydride, to convert same to acetic acid, followed by isolation and purification. This aftertreatment step requires a long time, during which time the obtained compound [4'] becomes partially decomposed. The present inventors conducted intensive studies to solve this problem associated with the aftertreatment step, as well as to improve yield. As a result, it has been found that, by adding acetic anhydride in advance in an amount (about 4 equivalents) necessary in the next step and by using dimethylaminopyridine in a toluene solvent in the presence of 0.25 equivalent of N-methylmorpholine, compound [4'] can be obtained. The obtained compound [4'] can be used in the next step without isolation or purification, and cyclization of compound [4'] using p-toluenesulfonic acid monohydrate resulted in the production of compound [5'] at a high yield (95–97%/o). Consequently, the yield of compound [5'] could be increased by about 40% as compared to A method.

Phosphorus oxychloride (POCl₃) used in Step 3 of A method is a toxic substance having high corrosiveness, so that the use thereof is under considerable restriction, which is greatly problematic for industrial use. The present inventors have found that p-toluenesulfonic acid monohydrate could afford safety and facilitated use, whereby an industrially utilizable production method was found.

Step 4

According to A method, compound [5'] is reacted with lithium aluminum hydride (LiAlH₄) in diethyl ether to give compound [6']. Both LilH₄ and diethyl ether used here are highly inflammable, posing problems of safety when they are used industrially. The present inventors have solved this problem by using sodium borohydride (NaBH₄) and tetrahydrofuran, as well as methanol as a reduction accelerator (activator), whereby a method for obtaining compound [6'] free of industrial problems has been established.

Surprisingly, the use of this method was also found to not only solve the problems of safety but also increase the yield to 85–95%. Consequently, the yield could be improved as compared to A method.

As the method to obtain the final compound [11'] from compound [6'], a method disclosed in WO95/18125 (hereinafter this method is to be referred to as B method) is most similar to the method of the present invention. The present inventors concretely considered B method.

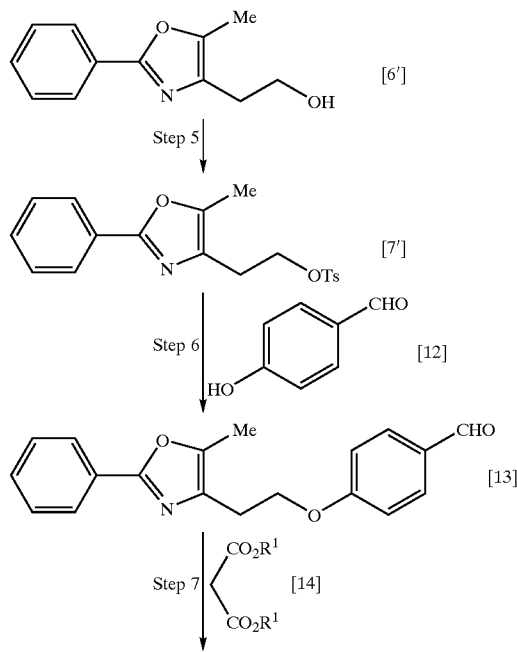

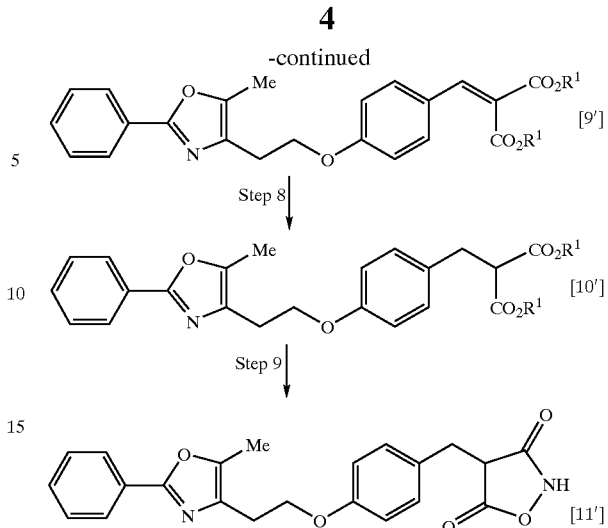

wherein R¹ is a lower alkyl.

Step 5

According to B method, compound [6'] is reacted with p-toluenesulfonyl chloride (TsCl) in dichloromethane in the presence of pyridine to give compound [7'].

Dichloromethane used as a solvent here is subject to great restriction of waste discharge when used in large amounts, as mentioned in Step 1 of A method, so that it is impractical in industrial production. The present inventors have found that the compound can be also efficiently reacted in toluene, which is safe, whereby this problem was solved.

As regards yield, B method accompanies, besides the objective compound [7'], compound [15]

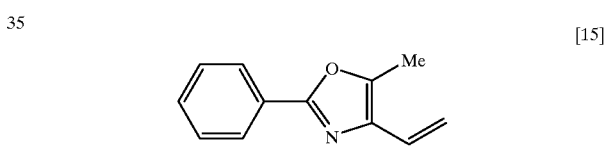

as a byproduct that reduces the yield of the objective compound [7']. To solve this problem, the method generally exemplified in the specification of WO95/18125, but not concretely disclosed as an example, was employed. To be specific, mesyl group was used as a leaving group instead of tosyl group. Namely, methanesulfonyl chloride (MsCl) instead of TsCl was reacted with compound [6'] to surprisingly afford the objective compound [7"]

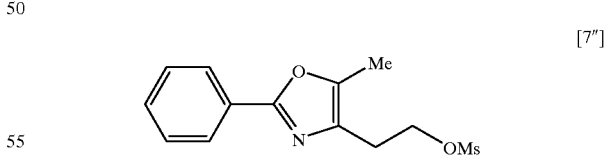

at a yield of 99–100%.

Step 6 and Step 7

In B method, compound [7'] is reacted with 4-hydroxybenzaldehyde [12] to give compound [13], and compound [13] is further reacted with malonic acid derivative [14] to give compound [9']. In this step, compound [13] is rather unstable and the yield of compound [9'] from compound [7'] was 65%, which is not at all satisfactory. The present inventors previously synthesized compound [8] from compound [12] and compound [14]

[8]

<chemical structure of compound [8]: 4-hydroxyphenyl CH=C(CO₂R¹)₂> wherein $R^1$ is as defined above, to improve the yield, and reacted the resulting compound and compound [7"] to find that compound [9'] could be obtained at a high yield (80–85%).

Step 8 and Step 9

In B method, compound [9'] is reduced under hydrogen atmosphere using a catalyst to give compound [10'], and compound [10'] is reacted with hydroxylamine in anhydrous alcohol to give the final objective compound [11']. According to this step, the yield (about 40%) of the final compound is not satisfactory. To increase the yield, the present inventors did not isolate compound [10'] but reacted the compound with hydroxylamine in a mixed solvent of tetrahydrofuran, water and alcohol, in the presence of a base (e.g., potassium carbonate, sodium carbonate or sodium methoxide) to give the objective compound [11'] at a high yield (80%).

While the foregoing relates to the method for producing compound [11'] from compound [6'], it is needless to say that compound [6'] is also useful for the production of the following compound [16]

[16]

<chemical structure of compound [16]> wherein X is oxygen atom or sulfur atom.

As mentioned-above, the present inventors studied the problems in each step in detail with the aim of improving the yield of the objective compound and establishing the method affording industrial production, they have found that the use of the above-mentioned solvent, base, catalyst and the like in each step results in the production of the objective compound at a high yield and also an industrially practical production method, which resulted in the completion of the present invention. That is, the present invention provides the following (1)–(7).

(1) A method for producing an isoxazolidinedione compound of the formula [11]

[11]

<chemical structure of compound [11]> wherein R is an optionally substituted aromatic hydrocarbon group, an optionally substituted alicyclic hydrocarbon group, an optionally substituted heterocyclic group or an optionally substituted condensed heterocyclic group, or a salt thereof, comprising the steps of (a) reacting compound [1]

[1]

<chemical structure of compound [1]: aspartic acid methyl ester> or a salt thereof with a compound of the formula [2]

[2]

<chemical structure of compound [2]: R-C(=O)-Cl> wherein R is as defined above, in the presence of an inorganic base in an aqueous solvent to give an aspartate derivative of the formula [3]

[3]

<chemical structure of compound [3]> wherein R is as defined above;

(b) reacting this compound with acetic anhydride using dimethylaminopyridine as a catalyst in the presence of a base, followed by heating for decarboxylation to give a compound of the formula [4]

[4]

<chemical structure of compound [4]> wherein R is as defined above;

(c) adding p-toluenesulfonic acid without isolating this compound to give an oxazolylacetate derivative of the formula [5]

[5]

<chemical structure of compound [5]> wherein R is as defined above;

(d) reducing this compound in tetrahydrofuran in the presence of $NaBH_4$ as a reducing agent and methanol as an activating agent to give an oxazolylethanol derivative of the formula [6]

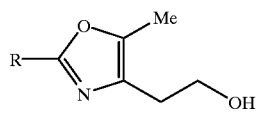

[6]

wherein R is as defined above;

(e) reacting this compound with mesyl chloride in toluene in the presence of triethylamine as a base catalyst to give a methanesulfonate derivative of the formula [7]

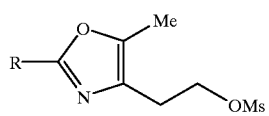

[7]

wherein R is as defined above;

reacting this compound with a compound of the formula [8]

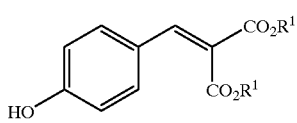

[8]

wherein $R^1$ is a lower alkyl, in the presence of potassium carbonate and a quaternary ammonium salt or tris[2-(2-methoxyethoxy)ethyl]amine as a catalyst to give a benzylidene derivative of the formula [9]

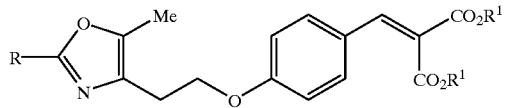

[9]

wherein R and $R^1$ is as defined above;

(g) reducing this compound under hydrogen atmosphere to give a malonic acid derivative of the formula [10]

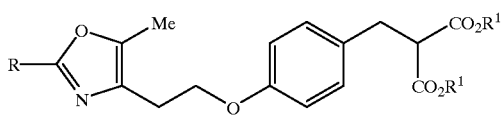

[10]

wherein R and $R^1$ is as defined above; and (h) reacting this compound with hydroxylamine in the presence of a base.

(2) A method for producing an oxazolylethanol derivative of the formula [6]

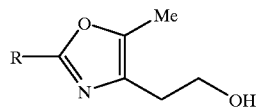

[6]

wherein R is as defined above, or a salt thereof comprising the steps of (a) reacting a compound [1]

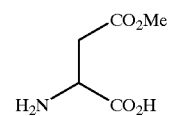

[1]

or a salt thereof in an aqueous solvent with a compound of the formula [2]

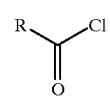

[2]

wherein R is as defined above, in the presence of an inorganic base to give an aspartate derivative of the formula [3]

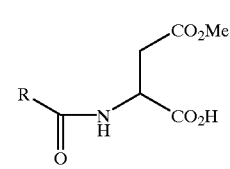

[3]

wherein R is as defined above;

(b) reacting this compound with acetic anhydride using dimethylaminopyridine as a catalyst in the presence of a base, followed by heating for decarboxylation to give a compound of the formula [4]

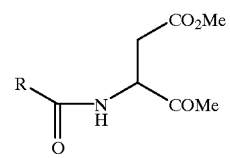

[4]

wherein R is as defined above;

(c) adding p-toluenesulfonic acid without isolating this compound to give an oxazolylacetate derivative of the formula [5]

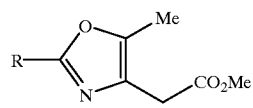

[5]

wherein R is as defined above; and
(d) reducing this compound in tetrahydrofuran in the presence of $NaBH_4$ as a reducing agent and methanol as an activating agent.

(3) A method for producing an aspartate derivative of the formula [3]

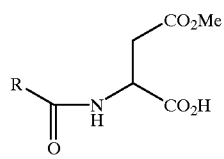

[3]

wherein R is as defined above, or a salt thereof, comprising reacting a compound [1]

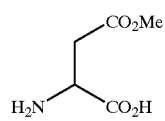

[1]

or a salt thereof with a compound of the formula [2]

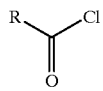

[2]

wherein R is as defined above, in an aqueous solvent in the presence of an inorganic base.

(4) A method for producing an oxazolylacetate derivative of the formula [5]

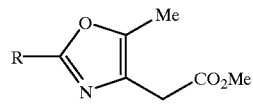

[5]

wherein R is as defined above, or a salt thereof, comprising reacting a compound of the formula [3]

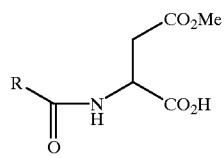

[3]

wherein R is as defined above, with acetic anhydride using dimethylamninopyridine as a catalyst in the presence of a base, heating for decarboxylation to give a compound of the formula [4]

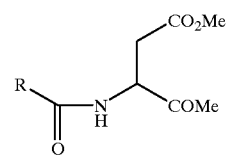

[4]

wherein R is as defined above, and adding p-toluenesulfonic acid without isolating this compound.

(5) A method for producing an oxazolylethanol derivative of the formula [6]

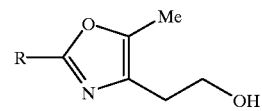

[6]

wherein R is as defined above, or a salt thereof, comprising reacting an oxazolylacetate derivative of the formula [5]

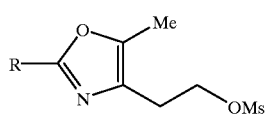

[5]

wherein R is as defined above, in tetrahydrofuran in the presence of $NaBH_4$ as a reducing agent and methanol as an activating agent.

(6) A method for producing a methanesulfonate derivative of the formula [7]

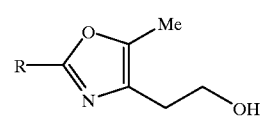

[7]

wherein R is as defined above, or a salt thereof, comprising reacting an oxazolylethanol derivative of the formula [6]

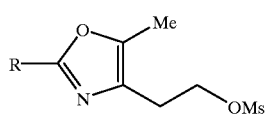

[6]

wherein R is as defined above, with mesyl chloride in toluene in the presence of triethylamine as a base catalyst.

(7) A method for producing a benzylidene derivative of the formula [9]

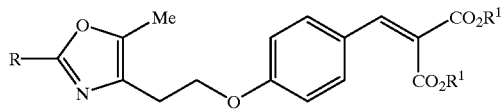

wherein R and $R^1$ are as defined above, or a salt thereof, comprising reacting a methanesulfonate derivative of the formula [7]

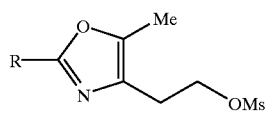

wherein R is as defined above, with a compound of the formula [8]

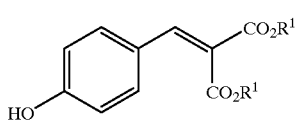

wherein $R^1$ is as defined above, in the presence of potassium carbonate and a quaternary ammonium salt or tris[2-(2-methoxyethoxy)ethyl]amine as a catalyst.

The terms used in the present specification are explained in the following.

The aromatic hydrocarbon group means phenyl, biphenylyl, naphthyl and the like. It may be an aralkyl group such as benzyl. Preferred is phenyl.

The alicyclic hydrocarbon group means alicyclic hydrocarbon group having 3 to 7 carbon atoms, and is exemplified by cyclopropyl, cyclobutyl, cyclopentyl, cyclohexyl, cycloheptyl, cyclopropenyl, cyclobutenyl, cyclobutadienyl, cyclopentenyl, cyclopentadienyl, cyclohexenyl, cyclohexadienyl, cycloheptenyl, cycloheptadienyl and the like, with preference given to alicyclic hydrocarbon group having 5 to 7 carbon atoms. Specific examples thereof include cyclopentyl, cyclohexyl, cycloheptyl, cyclopentenyl, cyclopentadienyl, cyclohexenyl, cyclohexadienyl, cycloheptenyl and cycloheptadienyl, with particular preference given to cyclopentyl and cyclohexyl.

The heterocyclic group is a 5- or 6-membered heterocycle having, as an atom constituting the ring, 1 to 3, preferably 1 or 2, hetero atoms selected from nitrogen atom, oxygen atom and sulfur atom, besides carbon atom, preferably an aromatic heterocycle. Specific examples thereof include thienyl, furyl, pyrrolyl, imidazolyl, pyrazolyl, thiazolyl, isothazolyl, oxazolyl, isoxazolyl, oxadiazolyl, thiadiazolyl, triazolyl, pyridyl, pyrazinyl, pyrimidinyl, pyridazinyl, triazinyl, dithiazolyl, dioxolanyl, dithiolyl, pyrrolidinyl, dithiadiazinyl, thiadiazinyl, morpholinyl, oxazinyl, thazinyl, piperazinyl, piperidinyl, pyranyl and thiopyranyl, with preference given to thienyl, furyl, pyrrolyl, imidazolyl, pyridyl and pyrmidinyl, and particular preference given to pyridyl, pyrimidinyl and imidazolyl.

The condensed heterocyclic group is a ring wherein 5- or 6-membered heterocycles having, as an atom constituting the ring, 1 to 3, preferably 1 or 2, hetero atoms selected from nitrogen atom, oxygen atom and sulfur atom, besides carbon atom, preferably aromatic heterocycles have been condensed, or a ring wherein such heterocycle, preferably an aromatic heterocycle, and a 4- to 6-membered aromatic hydrocarbon ring, preferably a benzene ring, have been condensed. Specific examples thereof include furoisoxazolyl, imidazothiazolyl, thienoisothiazolyl, thienothiazolyl, imidazopyrazolyl, cyclopentapyrazolyl, pyrrolopyrrolyl, cyclopentathienyl, thienothienyl, oxadiazolopyrazinyl, benzofumzanyl, thiadiazolopyridinyl, tnazolothiazinyl, triazolopyrimidinyl, triazolopyridinyl, benzotriazolyl, oxazolopyrimidinyl, oxazolopyridinyl, benzoxazolyl, thiazolopyridazinyl, thiazolopynmidinyl, benzisothiazolyl, benzothiazolyl, pyrazolotriazinyl, pyrazolothiazinyl, imidazopyrazolyl, purinyl, pyrazolopyridazinyl, pyrazolopyrimidinyl, imdazopyridinyl, pyranopyrazolyl, benzimidazolyl, indazolyl, benzoxathiolyl, benzodioxolyl, dithiolopyriridinyl, benzodithiolyl, indolidinyl, indolyl, isoindolyl, furopyrimidinyl, furopyridinyl, benzofuranyl, isobenzofuranyl, thienopyrazinyl, thienopyrimidinyl, thienodioxinyl, thienopyridinyl, benzothienyl, isobenzothienyl, cyclopentaoxazinyl, cyclopentafuranyl, benzothiadiazinyl, benzotriazinyl, pyridoxazinyl, benzoxazinyl, pyrimidothiazinyl, benzothiazinyl, pyrimidopyridazinyl, pyrmidopyrimidinyl, pyridopyridazinyl, pyridopyrimidinyl, cinnolinyl, quinazolinyl, quinoxalinyl, benzoxathiinyl, benzodioxinyl, benzodithiinyl, naphthyridinyl, isoquinolyl, quinolyl, benzopyranyl, benzothiopyranyl, chromanyl, isochromanyl, indolinyl and the like, with preference given to benzoxazolyl, benzisothiazolyl, benzothiazolyl, benzimidazolyl, indazolyl, benzoxathiolyl, benzodioxolyl, benzodithiolyl, indolyl, isoindolyl, benzofuranyl, isobenzofuranyl, benzothienyl, isobenzothienyl, benzothiadiazinyl, benzotriazinyl, benzoxazinyl, benzothiazinyl, cinnolinyl, quinazolinyl, quinoxalinyl, benzoxathiinyl, benzodioxinyl, benzodithiinyl, isoquinolyl, quinolyl, benzopyranyl, benzothiopyranyl, chromanyl, isochromanyl and indolinyl, and particular preference given to indolyl, isoindolyl, benzofuranyl, isobenzofuranyl, benzothienyl, isobenzothienyl, isoquinolyl and quinolyl.

The lower alkyl is a linear or branched alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, isohexl, 3,3-dimethylbutyl, 2,2-dimethylbutyl and the like, with preference given to alkyl having 1 to 4 carbon atoms such as methyl, ethyl, propyl, isopropyl, butyl, isobutyl, sec-butyl and tert-butyl, and particular preference given to methyl.

The optionally substituted means that the group may be substituted by 1 to 3 substituents which may be the same or different. Specific examples thereof include lower alkyl such as methyl, ethyl, propyl, butyl, tert-butyl and the like; lower alkoxy such as methoxy, ethoxy, propoxy, butoxy, tert-butoxy and the like; halogen atom; nitro; cyano; hydroxy; acyl (e.g., lower alkanoyl such as formyl, acetyl, propionyl, butyryl, isobutyryl and the like, aroyl such as benzoyl, naphthoyl and the like, and the like); acyloxy (acyl moiety being as defined above) such as formyloxy, acetyloxy, propionyloxy, butyryloxy, isobutyryloxy, benzoyloxy and the like; aralkyloxy such as benzyloxy, phenethyloxy, phenylpropyloxy and the like; mercapto; lower alkylthio such as methylthio, ethylthio, propylthio, butylthio, isobutylthio, tert-butylthio and the like; amino; lower alkylamino such as methylamino, ethylamino, propylamino, isopropylamino, butylamino and the like; di(lower)alkylamino such as dimethylamino, diethylamino, dipropylamino, diisopropylamino, dibutylamino and the like; carboxy, lower alkoxycarbonyl such as methoxycarbonyl, ethoxycarbonyl, propoxycarbonyl, isopropoxycarbonyl, butoxycarbonyl, tert-butoxycarbonyl and the like; acylamino (acyl moiety being as defined above); trifluoromethyl; phosphoryl; sulfonyl; sulfonyloxy; carbamoyl; sulfamoyl; lower alkylphosphonamide such as methylphosphonamide, ethylphosphonamide, propylphosphonamide, isopropylphosphonamide and the like; methylenedioxy; lower alkoxyphosphoryl such as methoxyphosphoryl, ethoxyphosphoryl, propoxyphosphoryl, isopropoxyphosphoryl and the like; lower alkylsulfonyl such as methylsulfonyl, ethylsulfonyl, propylsulfonyl, butylsulfonyl, tert-butylsulfonyl and the like; lower alkylsulfonylamino such as methylsulfonylamino, ethylsulfonylamino, propylsulfonylamino, butylsulfonylamino, tert-butyrylsulfonylamino and the like; and the like, with preference given to hydroxy, lower alkyl, lower alkoxy, aralkyloxy, mercapto, lower alkylthio, nitro, halogen atom, trifluoromethyl, amino, di(lower)alkylamino, lower alkylamino, acyl, cyano, carbamoyl, acyloxy, sulfonyl, carboxy and lower alkoxycarbonyl, and particular preference given to hydroxy, lower alkyl and lower alkoxy. As used herein, by lower is meant that the number of carbon atoms is preferably 1 to 6, more preferably 1 to 4.

The salts of the compounds of the formulas [3], [5]–[7], [9] and [11] may be any as long as they form nontoxic salts with the compounds of the above-mentioned formulas [3], [5]–[7], [9] and [11]. Specific examples thereof include alkali metal salts such as sodium salt, potassium salt and the like; alkaline earth metal salts such as magnesium salt, calcium salt and the like; ammonium salt; organic base salts such as trimethylamine salt, triethylamine salt, pyridine salt, picoline salt, dicyclohexylamine salt, N,N'-dibenzylethylenediamine salt and the like, and amino acid salts such as lysine salt, arginine salt and the like.

The salt of compound [1] may be any and includes, for example, inorganic acid addition salt such as hydrochloride, sulfate, phosphate, hydrobromide and the like; acid addition salt with organic acid such as oxalic acid, malonic acid, citric acid, fumaric acid, lactic acid, malic acid, succinic acid, tartaric acid, acetic acid, ascorbic acid, methanesulfonic acid, benzylsulfonic acid and the like; alkali metal salts such as sodium salt, potassium salt and the like; alkaline earth metal salts such as magnesium salt, calcium salt and the like; ammonium salt; organic base salt such as trimethylamine salt, triethylamine salt, pyridine salt, picoline salt, dicyclohexylamine salt, N,N'-dibenzylethylenediamine salt and the like; and the like.

In the following, the production method of compound [11] and an intermediate compound is described in detail.

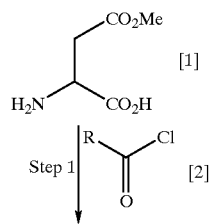

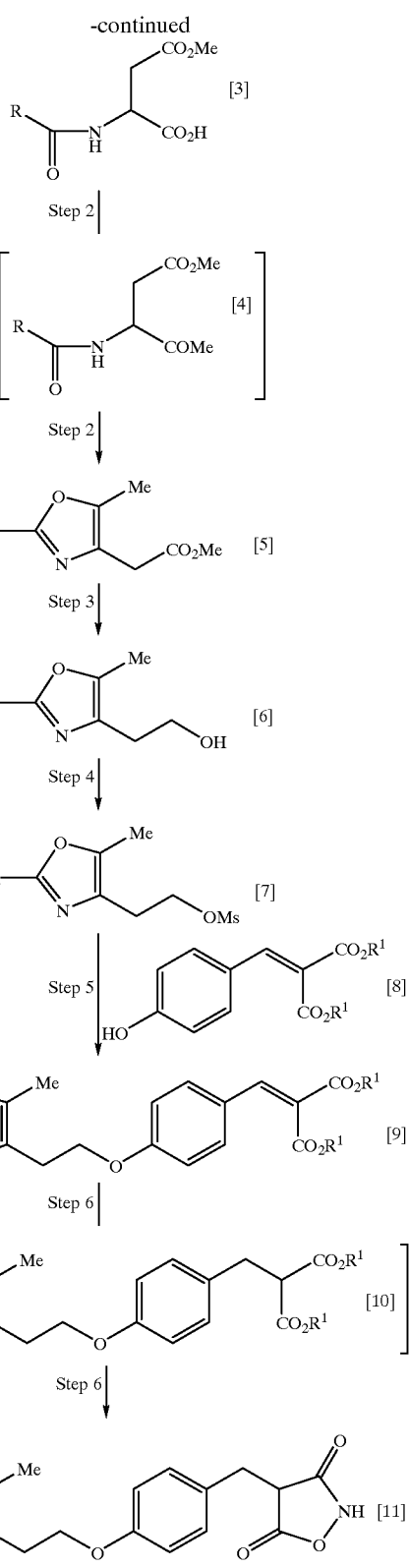

wherein R and $R^1$ are as defined above.

General Production Method

Step 1

Compound [1] or a salt thereof is reacted with compound [2] in an aqueous solvent in the presence of an inorganic base to give compound [3].

The aqueous solvent to be used for the reaction is specifically water which may contain a polar solvent, such as methanol, ethanol, acetic acid and the like, in an amount which does not interfere with the reaction.

The inorganic base is potassium carbonate, sodium carbonate, potassium hydrogencarbonate, sodium hydrogencarbonate, sodium hydroxide, potassium hydroxide and the like, with preference given to sodium carbonate.

The reaction temperature is −20° C.–50° C., preferably 0° C.–30° C. The reaction time is 2–24 hours, preferably 2–5 hours.

Step 2

Compound [4] can be obtained by reacting compound [3] with acetic anhydride in an organic solvent in the presence of a base and using a catalyst, followed by heating. The obtained compound is cyclized by adding an acid such as p toluenesulfonic acid and the like, without isolation, whereby compound [5] can be obtained.

Preferable organic solvent to be used for the reaction is toluene. To proceed to the next reaction without isolating compound [4], the amount necessary for the next reaction, preferably about 4 equivalents, of acetic anhydride is used.

The base is exemplified by tertiary amine. Preferred is N-methylmorpholine or pyridine and more preferred is N-methylmorpholine. The base is preferably used in an amount of 0.25–1.0 equivalent.

The catalyst is preferably dimethylaminopyridine.

The acid necessary for obtaining compound [5] from compound [4] is preferably p-toluenesulfonic acid monohydrate.

The heating temperature of decarboxylation is 40° C.–70° C., preferably 55° C.–60° C. The reaction time of decarboxylation is 4–48 hours, preferably 4–24 hours.

The reaction temperature of cyclization is 70° C.–100° C., preferably 85° C.–90° C. The reaction time of cyclization is 2–24 hours, preferably 4–6 hours.

Step 3

Compound [5] is reduced in a solvent using a reducing agent to give compound [6]. By using an activating agent for the reducing agent, the reaction can proceed smoothly.

The solvent to be used for the reaction is preferably tetrahydrofuran.

The reducing agent is preferably sodium borohydride (NaBH$_4$).

The activating agent for the reducing agent is preferably methyl alcohol.

The reaction temperature is 30° C.–100° C., preferably 40° C.–80° C. The reaction time is 1–10 hours, preferably 1–2 hours.

Step 4

Compound [6] is reacted with methanesulfonyl chloride (mesyl chloride) in a solvent in the presence of a base to give compound [7].

The solvent to be used for the reaction is preferably organic solvent such as toluene, dichloromethane and the like, with preference given to toluene.

The base is exemplified by tertiary amine. Preferred is triethylamine and N-methylmorpholine, with particular preference given to triethylamine.

The reaction temperature is 0° C.–100° C., preferably 0° C.–50° C. The reaction time is 0.5–24 hours, preferably 1–10 hours.

Step 5

Compound [7] is reacted with compound [8] in a solvent in the presence of a base and using a catalyst to give compound [9].

The solvent to be used for the reaction is preferably toluene.

Preferred base is potassium carbonate.

The catalyst is a quaternary ammonium salt such as tetrabutylammonium bromide, tetraethylammonium bromide, tetraethylammonium bromide, tetraethylammonium chloride, benzyltrimethylammonium chloride, benzyltriethylammonium chloride, benzyltriethylammonium bromide and the like, or tris[2-(2-methoxyethoxy)ethyl]amine, with preference given to tetrabutylammonium bromide and tris[2-(2-methoxyethoxy)ethyl]amine.

The reaction temperature is 0° C.–150° C., preferably 10° C.–120° C. The reaction time is 5–24 hours, preferably 6–10 hours.

Step 6

Compound [9] is reduced under hydrogen atmosphere in a solvent using a reducing catalyst to give compound [10]. Without isolation, this compound is reacted with hydroxylamine in a solvent in the presence of a base from under cooling to heating to give compound [11].

The solvent to be used for the reaction is an organic solvent such as methanol, ethanol, propanol, isopropanol, tetrahydrofuran, dioxane, dichloromethane, acetic acid and the like, or a mixed solvent thereof, which is preferably tetrahydrofuran.

The reducing catalyst is palladium carbon, palladium black and the like, which is preferably palladium carbon.

The reaction time of reduction is 4–24 hours, preferably 6–10 hours.

The solvent to be used for the reaction of from compound [10] to compound [11] is methanol, ethanol, propanol, isopropanol, tetrahydrofuran, dioxane, dichloromethane, acetic acid, water and the like, or a mixed solvent thereof. Preferred is a mixed solvent of methanol, tetrahydrofuran and water.

The base is, for example, potassium carbonate, sodium carbonate, sodium methoxide or sodium ethoxide. Preferred is potassium carbonate.

The reaction temperature is 0° C.–50° C., preferably 20° C.–30° C. The reaction time is 4–24 hours, preferably 6–10 hours.

EXAMPLE

Example 1

Production of β-methyl N-benzoyl-L-aspartate (Compound [3] (R=phenyl))

β-Methyl L-aspartate hydrochloride (compound [1]; 183.6 g) was dissolved in water (800 mL). This solution was cooled to 5° C. while stirring and a solution of sodium carbonate (265 g) in water (1 L) was added. To this reaction mixture was added benzoyl chloride (121.9 mL) at 5° C. over 1 hr 20 min. After stirring at 10° C.–18° C. for 2 hours, water (1.2 L) was added to the reaction mixture and the reaction mixture was made homogeneous. Thereto was added dichloromethane (0.5 L) to partition the solution and the organic layer was removed. Conc. hydrochloric acid was added to the aqueous layer to adjust to pH=2, and ethyl acetate (1.5 L) was added and extracted. The aqueous layer was further extracted with ethyl acetate (0.5 L) and the organic layers were combined. The organic layer was washed successively with water (1 L) and saturated brine (1 L) and dried over anhydrous magnesium sulfate. After filtration, the filtrate was concentrated under reduced pressure to about half the amount and the precipitated crystals were collected by filtration. The filtrate was further concentrated under reduced pressure to about half the amount and the precipitated crystals were collected by filtration. The obtained crystals were dried to give the title compound (compound [3]; 229.9 g, yield 91.5%).

m.p. 124–125° C.

$^1$H-NMR (300 MHz, DMSO-d$_6$, TMS) δ2.80 (1H, dd, J=16.2, 8.1 Hz), 2.94 (1H, dd, J=16.2, 6.3 Hz), 3.61 (3H, s), 4.79 (1H, m), 7.45–7.58 (3H, m), 7.83–7.86 (2H, m), 8.77 (1H, d, J=7.8 Hz), 12.82 (1H, br-s)

FAB-MS: 252.1 (M+H)+

Example 2

Production of methyl 2-(5-methyl-2-phenyl-4-oxazolyl)acetate (Compound [5] (R=phenyl))

To β-methyl N-benzoyl-L-aspartate (compound [3]; 229.9 g) obtained in Example 1 were successively added toluene (1.2 L), acetic anhydride (346 mL), N-methylmorpholine (4.7 mL) and 4-dimethylaminopyridine (1.04 g) and the mixture was stirred at internal temperature of 55–60° C. for 4 hr to give a solution of methyl 3-benzoylamino-4-oxopentanoate (compound [4]) in toluene. Without isolating compound [4], p-toluenesulfonic acid monohydrate (31.8 g) was added to this solution of methyl 3-benzoylamino4-oxopentanoate (compound [4]) in toluene. The mixture was stirred at 85–90° C. for 5 hr and cooled to room temperature. To the reaction mixture was added, with stirring, an aqueous solution of sodium carbonate (75.6 g) in water (303 mL), and the mixture was adjusted to pH 7–7.5. After standing still, the aqueous layer was removed and the organic layer was concentrated to give the title compound (compound [5]; 206.7 g, yield 97.71%).

Example 3

Production of 2-(5-methyl-2-phenyl-4-oxazolyl) ethanol (Compound [6] (R=phenyl))

Methyl 2-(5-methyl-2-phenyl-4-oxazolyl)acetate (compound [5]; 170 g) obtained in Example 2 was dissolved in tetrahydrofuran (935 mL) and sodium borohydride (27.81 g) was added at room temperature. This suspension was heated to 60° C. and stirred, and methyl alcohol (57.9 mL) was added dropwise over 1 hr. After dropwise addition, the reaction mixture was cooled to room temperature and water (35 mL) was added dropwise. The mixture was stirred at room temperature for 1 hr and filtered to remove solid components. The solid components were washed with tetrahydrofuran and the washing was combined with the previous filtrate, which was followed by concentration under reduced pressure. Ethyl acetate (1 L) was added to the residue and after dissolution, water (1 L) was added for partitioning. The aqueous layer was again extracted with ethyl acetate (0.5 L), and the organic layers were combined and washed successively with saturated sodium hydrogencarbonate solution (1 L) and saturated brine (1 L) and dried over anhydrous magnesium sulfate. After filtration, the filtrate was concentrated under reduced pressure to give crude crystals (compound [6]; 149 g). The crystals were recrystallized from a mixed solvent of n-hexane (1 L) and ethyl acetate (0.2 L) to give the title compound (compound [6]; 134 g, yield 89.7%).

m.p. 73.0–73.8oC $^1$H-NMR (300 MHz, CDCl$_3$, TMS) δ2.34 (3H, s), 2.72 (2H, t, J=5.4 Hz), 3.27 (1H, br-s), 3.92 (2H, t, J=5.4 Hz), 7.38–7.47 (3H, m), 7.95–7.99 (2H, m)

IR (KBr) 3294, 1647, 1556, 1447, 1338, 1056, 778, 715,691 cm$^{-1}$

FAB-MS: 204.1 (M+H)+

Example 4

Production of 2-(5-methyl-2-phenyl-4-oxazolyl) ethyl methanesulfonate (Compound [7] (R=phenyl))

2-(5-Methyl-2-phenyl-4-oxazolyl)ethanol (compound [6]; 108.6 g) obtained in Example 3 was dissolved in toluene (600 mL), and methanesulfonyl chloride (45.4 mL) was added, which was followed by stirring under ice-cooling. To this solution was added dropwise triethylamine (81.7 mL) under ice-cooling. After stirring for 1 hr, toluene (1 L) was added and 1N hydrochloric acid (1 L) was added for partitioning. The aqueous layer was extracted again with toluene (0.5 L). The combined organic layers were washed successively with water (1 L), saturated sodium hydrogencarbonate solution (1 L) and saturated brine (1 L), and dried over anhydrous magnesium sulfate. The desiccant was filtered off and the filtrate was concentrated under reduced pressure to give the title compound (compound [7]; 150 g, yield 100%) as crystals.

m.p. 88.2–89.0° C.

$^1$H-NMR (300 MHz, CDCl$_3$, TMS) δ2.36 (3H, s), 2.96 (3H, s), 2.96 (2H, t, J=6.6 Hz), 4.53 (2H, t, J=6.6 Hz), 7.39–7.47 (3H, m), 7.94–7.99 (2H, m)

IR (KBr): 1637, 1340, 1160, 981, 961, 869, 692 cm$^{-1}$

FAB-MS: 282.1 (M+H)+

Preparation Example 1

Production of dimethyl 2-(4-hydroxybenzylidene) malonate (Compound [8])

To a mixture of 4-hydroxybenzaldehyde (280.9 g), dimethyl malonate (289.2 mL) and toluene (1.12 mL) were successively added acetic acid (13.2 mL) and piperidine (11.4 mL). After dehydration under refluxing at internal temperature of 70° C.–75° C. for about 4 hr, the mixture was cooled to internal temperature of not more than 10° C. and stirred further for 1 hr. The precipitated crystals were collected by filtration and washed with toluene (350 mL) to give the title compound (compound [8]; 523.7 g, yield 96.4%)., m.p. 157.4–158.0° C.

$^1$H-NMR (300 MHz, CDCl$_3$, TMS) δ3.84 (3H, s), 3.87 (3H, s), 5.71 (1H, m), 6.81–6.84 (2H, m), 7.26–7.34 (2H, m), 7.70 (lH, s)

IR (KBr): 3340, 1740, 1670, 1320, 1070, 840 cm$^{-1}$

Example 5

Production of dimethyl [4-[2-(5-methyl-2-phenyl-4-oxazolyl)ethoxy]benzylidene]-malonate (Compound [9] (R=phenyl, R$^1$=methyl))

2-(5-Methyl-2-phenyl-4-oxazolyl)ethyl methanesulfonate obtained in Example 4 (compound [7]; 24.4 g) and dimethyl 2-(4-hydroxybenzylidene)malonate obtained in Preparation Example 1 (compound [8]; 20.5 g) were mixed with tetrabutylammonium bromide (1.4 g) and toluene (210 mL). The mixture was heated to 90° C. and dissolved. Then potassium carbonate (13.2 g) was added and the mixture was stirred at 110° C. for 6 hr. The reaction mixture was ice-cooled and water (210 mL) was added, which was followed by stirring. After standing still, the aqueous layer was removed and 10% aqueous sodium chloride solution (210 mL) was added to the organic layer with stirring. The reaction mixture was allowed to stand and the aqueous layer was removed. The organic layer was concentrated and the concentrated residue was dissolved in methanol (150 mL) under heating. The reaction mixture was cooled to 10° C. or less and the reaction mixture was stirred for 1 hr. The obtained crystals were collected by filtration and washed with methanol (65 mL) to give the title compound (compound [1]; 31.1 g, yield 85.0%).

m.p. 104.0–105.0° C.

$^1$H-NMR (300 MHz, CDCl$_3$, TMS) δ2.37 (3H, s), 2.99 (2H, t, J=6.7 Hz), 3.82 (3H, s), 3.85 (3H, s), 4.28 (2H, t, J=6.7 Hz), 6.89 (2H, d, J=6.8 Hz), 7.35–7.43 (5H, m), 7.70 (1H, s), 7.97 (2H, m)

IR (KBr): 1729, 1706, 1606, 1252, 1066 cm$^{-1}$

FAB-MS: 422.1 (M+H)+

Example 6

Production of 4-[4-[2-(5-methyl-2-phenyl-4-oxazolyl)ethoxy]benzyl]-3,5-isoxazolidinedione (Compound [11] (R=phenyl))

Dimethyl [4-[2-(5-methyl-2-phenyl-4-oxazolyl)ethoxy]benzylidene]-malonate (compound [9]; 2.5 g) obtained in Example 5 was dissolved in tetrahydrofuran (20 ml) and 5% Pd-C (150 mg) was added. The mixture was vigorously stirred under hydrogen atmosphere at normal temperature and normal pressure. After 8 hr, the catalyst was filtered off and hydroxylamine (360 mg), methanol (4 ml) and potassium carbonate (574 mg) were added to the filtrate. Water (4 ml) was added dropwise and the mixture was stirred at room temperature for 6 hr.

The solvent was evaporated and 1N aqueous HCl solution (50 ml) was added to the residue for acidification. The mixture was extracted twice with ether and dried over magnesium sulfate. The solvent was evaporated and the obtained solid was recrystallized twice from methanol to give the title compound (compound [11]; 650 mg, yield 80%).

Industrial Applicability

As is evident from the above, the method of the present invention enables extremely efficient production of a compound of the formula [11] and an intermediate compound thereof, that are useful as therapeutic agents for diabetes, at high yield, as compared to conventional methods. The production method of the present invention is highly practical and industrially very useful.

This application is based on application no. 104098/1998 filed in Japan, the content of which is incorporated hereinto by reference.

What is claimed is:

1. A method for producing an oxazolylethanol derivative of the formula

[6]

wherein R is an optionally substituted aromatic hydrocarbon group, an optionally substituted alicyclic hydrocarbon group, an optionally substituted heterocyclic group or an optionally substituted condensed heterocyclic group, or a salt thereof, comprising the steps of
(a) reacting a compound [1]

[1]

or a salt thereof in an aqueous solvent with a compound of the formula [2]

[2]

wherein R is as defined above, in the presence of an inorganic base to give an aspartate derivative of the formula [3]

[3]

wherein R is as defined above;
(b) reacting this compound with acetic anhydride using dimethylaminopyridine as a catalyst in the presence of a base, followed by heating for decarboxylation to give a compound of the formula [4]

[4]

wherein R is as defined above;
(c) adding p-toluenesulfonic acid without isolating this compound to give an oxazolylacetate derivative of the formula [5]

[5]

wherein R is as defined above;
(d) reducing this compound in tetrahydrofuran in the presence of NaBH$_4$ as a reducing agent and methanol as an activating agent.

* * * * *